United States Patent [19]
Kumar et al.

[11] Patent Number: 5,135,604
[45] Date of Patent: Aug. 4, 1992

[54] ANALYSIS OF RADIOFREQUENCY DISCHARGES IN PLASMA

[75] Inventors: Devendra Kumar; Sean P. McGlynn, both of Baton Rouge, La.

[73] Assignee: Board of Supervisors of Louisiana State University and Agricultural and Mechanical College, Baton Rouge, La.

[21] Appl. No.: 621,784

[22] Filed: Dec. 4, 1990

[51] Int. Cl.[5] ............... H01L 21/306; B44C 1/22; C23C 14/00
[52] U.S. Cl. .................. 156/626; 118/712; 156/643; 156/345; 204/192.33; 356/316
[58] Field of Search ............ 156/626, 627, 643, 345; 204/192.13, 192.33, 298.03, 298.32; 118/712, 50.1, 620; 356/316, 319, 346, 437; 427/8, 10, 38, 39; 219/121.4, 121.41, 121.83

[56] References Cited
PUBLICATIONS

D. Kumar, et al., "Time-resolved laser optogalvanic spectroscopy of iodine in a radio frequency discharge," J. Chem. Phys., vol. 90, pp. 4008-4014 (1989).
Haner, et al., "Time-Resolved Study of the Laser Optogalvanic Effect in $I_2$," Chem. Phys. Lett., vol. 96 (3), pp. 302-306 (1983).
Uetani, et al., "Temporal Variation of Electron Density in a Laser-Perturbed Discharge Plasma and its Relationship to the Optogralvanic Signal," Optics Comm., vol. 49 (4), pp. 258-262 (1984).
Kumar, et al., "Photoacoustics using radio-frequency laser-optogalvanic detection: a new technique for low-pressure photoacoustic spectroscopy, Magnetic predissociation of the $\bar{B}$ state of $I_2$," Can. J. Phys., vol. 64, pp. 1107-1110 (1986).

Primary Examiner—William A. Powell
Attorney, Agent, or Firm—John H. Runnels

[57] ABSTRACT

Separation of laser optogalvanic signals in plasma into two components: (1) an ionization rate change component, and (2) a photoacoustic mediated component. This separation of components may be performed even when the two components overlap in time, by measuring time-resolved laser optogalvanic signals in an rf discharge plasma as the rf frequency is varied near the electrical resonance peak of the plasma and associated driving/detecting circuits. A novel spectrometer may be constructed to make these measurements. Such a spectrometer would be useful in better understanding and controlling such processes as plasma etching and plasma deposition.

10 Claims, 8 Drawing Sheets

ANALYSIS OF RADIOFREQUENCY DISCHARGES IN PLASMA

STATEMENT REGARDING FEDERALLY SPONSORED RESEARCH

The development of this invention was partially funded by the Government under grant DE-FG05-87ER60503 awarded by the Department of Energy. The Government may have certain rights in this invention.

BACKGROUND OF THE INVENTION

This invention pertains to laser optogalvanic signals in plasma, particularly to the separation of two different components comprising such signals: photoacoustic mediated effects, and ionization rate change effects.

Plasmas are used extensively in a number of industrial or manufacturing processes, such as depositing diamond films, depositing other thin films, semiconductor manufacture, plasma etching, and deposition of coatings for a variety of purposes. Because of its complexity, plasma characteristics are incompletely known. The mechanisms of depositions, etchings, coatings, etc. are not well understood.

Plasmas generated at high rf frequencies (more than a few MHz) are generally better suited in applications in etching and deposition. However, there are serious problems in analyzing or measuring such high rf plasmas. Consequently, such plasma manufacturing processes are currently used with incomplete knowledge of important plasma characteristics, such as electron and ion temperatures, plasma potential, and the nature of the ions interacting with the surface of the substrate material. This incomplete knowledge precludes proper understanding of etching and deposition processes. Therefore, plasma etching and deposition processes are currently used in a somewhat hit-or-miss manner with different gases, gas mixtures, rf frequencies, and powers.

The laser optogalvanic (LOG) effect is the change of the electrical impedance of a plasma caused by resonant absorption of laser radiation in the plasma. The absorption of laser radiation by a plasma species disturbs the dynamic equilibrium of the various plasma processes (e.g., absorption/emission, collisional excitation/deexcitation, ionization/recombination, etc.), and thus produces a LOG signal.

The laser optogalvanic effect has been used for some time to study rf discharges in plasma. Better understanding of plasma characteristics should enhance the quality or rate of plasma manufacturing processes. Because present optogalvanic methods do not extract the "true" optogalvanic signal (i.e., the ionization rate change component), they are of limited analytical use.

In our recent work on the LOG effect in rf discharges in iodine, it was found that LOG signals were generated by two distinct mechanisms: (i) equilibrium ionization rate changes (IRC); and (ii) a photoacoustic (PA) effect. Kumar et al., "Time-Resolved Laser Optogalvanic Spectroscopy of Iodine in a Radio Frequency Discharge," J. Chem. Phys., Vol. 90 (8), pp. 4008–4014 (1989). It was shown that thermal effects and ionization rate changes are not involved in the final step of PA-mediated LOG signal generation. Instead, it was found that the pressure wave generated by a PA effect produced the LOG signals by an actual physical movement of the charged species in the "sensitive" region of the discharge. Iodide ions have very small mobility compared to electrons, and at an rf frequency of ~30 MHz, the ions oscillate about their mean positions with a small displacement amplitude. In iodine, for low power discharge, the sensitive regions are therefore confined to the vicinity of the rf electrodes. This region can be identified as positive-ion sheaths that are perturbed by the PA wave. These PA-mediated LOG signal components were easily identified by the acoustic wave transit time delay from the region of laser excitation to the rf electrode(s). Laser-induced direct photoionization or collision-assisted photoionization, on the other hand, generated a nearly synchronous change in discharge conductivity and, consequently, a fast LOG signal component. The fast and the slow LOG signal components in iodine, being separated in time, were distinguished and identified. This reference does not, however, disclose or suggest means for resolving the IRC and PAM components when those two components overlap in time. (For simplicity, we will use the abbreviation IRC to refer to LOG signals, or components of LOG signals, generated by ionization rate changes, and PAM to refer to photoacoustically mediated LOG signals or components.)

In general, the PAM and IRC components of a LOG signal overlap in time, and a complex signal profile results. For example, neon atoms are much lighter than iodine, and the "sensitive" region can be spatially diffuse. A laser beam, therefore, propagates through the "sensitive" region of the discharge, and a complex LOG signal profile results.

To the knowledge of the inventors, no prior reference discloses or suggests a means for resolving IRC and PAM components of a LOG signal where those signal components overlap in time. Such overlap can be caused, for example, when the sensitive region is diffused throughout the discharge.

Haner et al., "Time-Resolved Study of the Laser Optogalvanic Effect in $I_2$," Chem. Phys. Lett., Vol. 96 (3), pp. 302–306 (1983) discloses that a photoacoustic effect can be a component of a laser optogalvanic signal.

Uetani et al., "Temporal Variation of Electron Density in a Laser-Perturbed Discharge Plasma and its Relationship to the Optogalvanic Signal," Optics Comm., Vol. 49 (4), pp. 258–262 (1984) discloses that the resonance frequency of a plasma in an rf-discharge may be shifted by laser irradiation.

SUMMARY OF THE INVENTION

We have discovered a new technique that allows separation of LOG signals into their IRC and PAM components, even when both types of signal components overlap in time. Dramatic changes occur in the temporal profiles of LOG signals produced by pulsed laser excitation as the rf frequency is varied near the electrical resonance peak of the plasma with the associated driving/detecting circuits. Observation of these changes permits separation of the IRC and PAM components.

This novel technique allows a better understanding of radiofrequency plasmas, particularly in the "sheath" region of the plasma near the electrodes, a region which plays a critical role in etching and deposition processes. This better understandings should, in turn, permit the manufacture of better finished products.

The novel technique may also be used to construct novel instruments to study radiofrequency discharges in plasmas. By resolving the IRC and PAM components of a LOG signal, it is now possible to build a spectrometer which can yield "true" optogalvanic spectra—i.e., spectra resolved into IRC and PAM components. Such a spectrometer should be useful in chemical analysis of rf plasmas.

DETAILED DESCRIPTION OF THE INVENTION

The experimental apparatus for LOG measurements was substantially as described in Kumar et al., "Time-Resolved Laser Optogalvanic Spectroscopy of Iodine in a Radio Frequency Discharge," J. Chem. Phys., Vol. 90 (8), pp. 4008-4014 (1989); and Kumar et al., "Photoacoustics using Radio-Frequency Laser-Optogalvanic Detection: A New Technique for Low Pressure Photoacoustic Spectroscopy," Can. J. Phys., Vol. 64, pp. 1107-1110 (1986); the entire disclosures of both of which are incorporated by reference.

Figure 1:
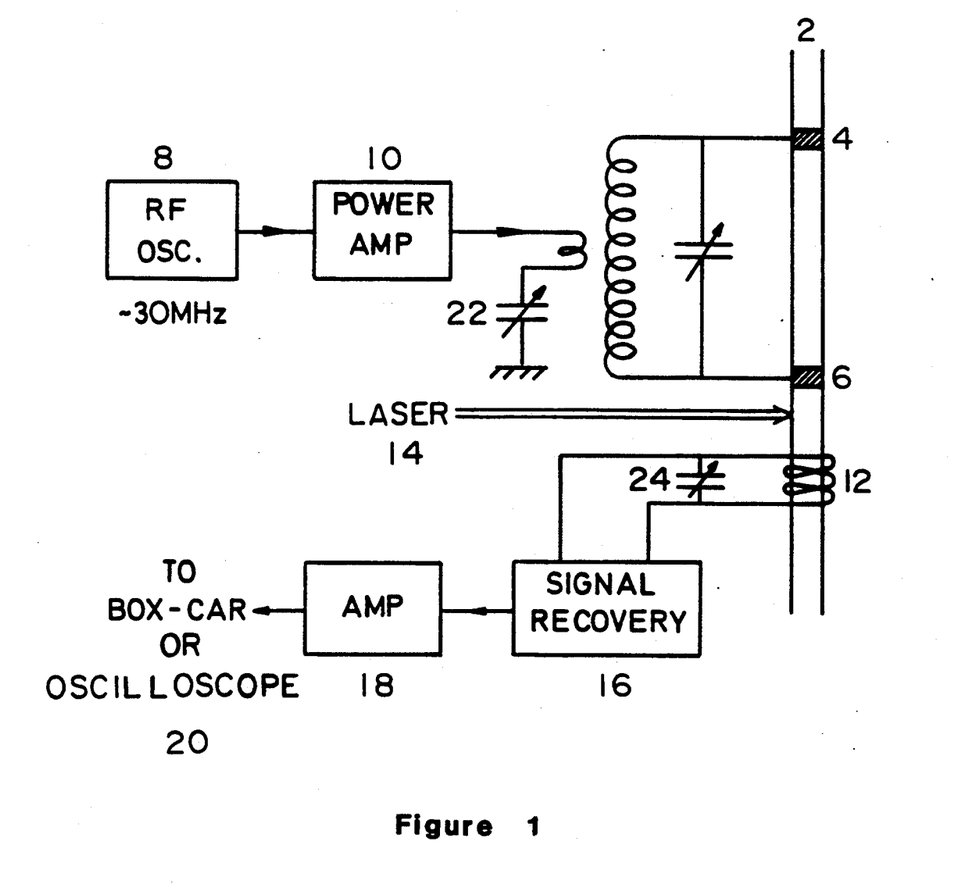
FIG. 1 illustrates the experimental setup for laser optogalvanic (LOG) study of a radiofrequency discharge plasma.

As illustrated in FIG. 1, the sample was contained in quartz discharge cell 2, two cm in diameter and thirty cm long. Two copper electrodes 4 and 6, each wound around the exterior of cell 2, were positioned about 5 cm apart. An rf oscillator 8 and amplifier 10 served as a $\sim 30$ MHz source of rf power. The rf voltage was resonantly stepped-up and applied to external electrodes 4 and 6. An rf power of 0.1-0.2 W was sufficient to sustain a stable, low-noise discharge in neon at $\sim 5$ torr pressure.

Resonantly tuned pick-up coil 12, also wound around discharge cell 2, was situated $\sim 1$ cm below the lower rf electrode 6 and coupled to the rf discharge, which extended beyond electrodes 4 and 6. The output of pulsed, tunable dye laser 14 impinged transversely on cell 2 at a point between electrode 6 and pick-up coil 12. When laser 14 was tuned to a frequency absorbed by a species in the discharge, a change occurred in the rf power transferred to pick-up coil 12. This change constituted the optogalvanic signal. This signal was recovered by demodulation in signal-recovery section 16, and after amplification by amplifier 18, was sent to oscilloscope or box-car 20 for visual monitoring or for recording. It is also possible to eliminate pickup coil 12, and use the rf circuit itself as its own detector.

A convenient alternative to this sample cell was found to be a commercially available hollow cathode lamp with a long neck ($\sim 6$ cm) filled with neon ($\sim 5$ torr). (Beckman Instruments, Part No. 180181). The internal electrodes, being relatively far from the rf electrodes and from the pick-up coil placed around the neck, did not substantially interfere with the rf discharge. In this case, the distance between electrodes 4 and 6 was reduced to $\sim 2$ cm. Most measurements described below used such a commercially available hollow cathode lamp.

The rf circuit was initially tuned as follows: With the discharge on, at a given power amplifier gain, the oscillator frequency and tuning capacitor 22 associated with the primary of the step-up transformer were adjusted to find the maximum rf power meter "dip." This dip indicated resonance in the driving circuit. Tuning capacitor 24 associated with pick-up coil 12 was then adjusted for maximum "pick-up," as indicated by a rectified DC maximum. Even though pick-up coil 12 put a negligible load on the rf discharge, it is then preferred to recheck the resonance in the driving circuit. Indeed, because the driving circuit resonance was slightly dependent on the rf power, it should finally be fine-tuned when the discharge attains stability. The resonance frequency is denoted $f_o$.

A flash-lamp pumped dye laser (Chromatix CMX-4, $\sim 1$ μs pulse width, resolution $\sim 0.1$ cm$^{-1}$, beam focused to $<0.5$ mm diameter) was used to excite various $1s_j \rightarrow 2p_k$ transitions in the neon. The resulting LOG signal profiles were recorded with the rf frequency f: (1) set at $f_o$, (2) set slightly below $f_o$, and (3) set slightly above $f_o$. Changes in LOG signal profile were also monitored as the rf frequency was scanned across the driving circuit resonance peak. Finally, with the laser off, the rf resonance profile was recorded by scanning f, and recording the DC voltage in the demodulator of the signal-recovery section.

Figure 2:
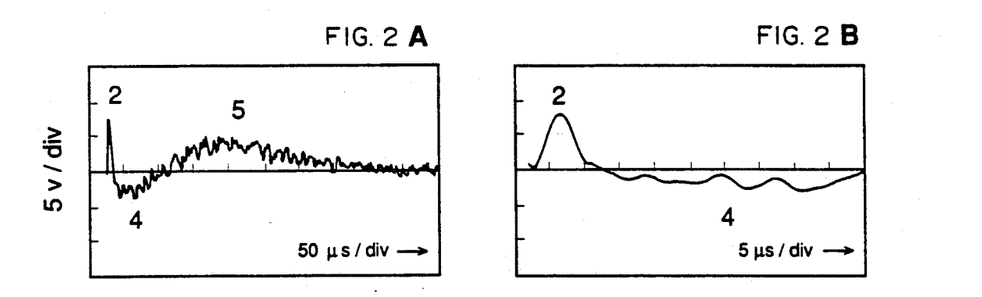
FIGS. 2A-H illustrate temporal evolution of LOG signals in an rf discharge in neon, at or on either side of the rf resonance frequency.
Figure 2E:
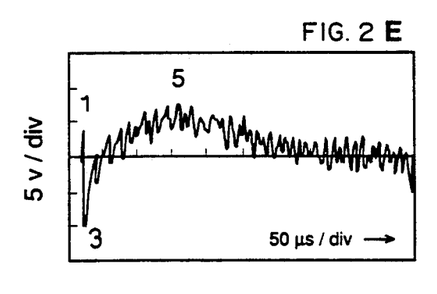
Figure 2F:
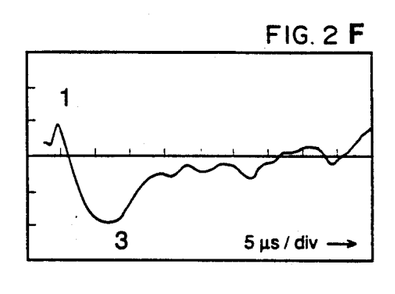
Figure 2G:
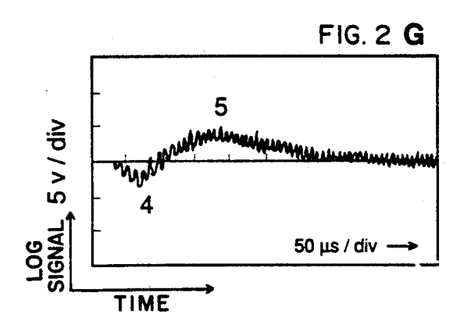
Figure 2H:
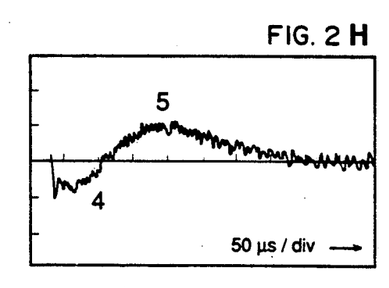

LOG signals from several $1s_j \rightarrow 2p_k$ neon transitions were studied in the excitation range 15,000-17,000 cm$^{-1}$. The temporal profiles of the faster components of these signals were extremely sensitive to changes in rf frequency near $f = f_o$. While the temporal profiles of the LOG signals from different neon transitions may differ because of their dependence upon $1s_j$ population densities, from which the excitation occurs, and upon the decay branching ratios of the terminal $2p_k$ levels, their overall shapes varied in systematic fashion with rf frequency. These changes fell into a pattern illustrated in FIGS. 2A-H for the transition $1s_5 \rightarrow 2p_2$ (16,996.61 cm$^{-1}$). FIGS. 2A-H illustrate the temporal evolution of LOG signals in an rf discharge in $\sim 5$ torr neon, with the rf frequency set at, or on either side of, the resonance frequency $f_o = 29.24$ MHz. Only the $1s_5 \rightarrow 2p_2$ transition is shown in FIGS. 2A-H. (Similar effects were observed for other $1s_j \rightarrow 2p_k$ transitions). In FIGS. 2A and 2B, $f = f_o = 29.24$ MHz. In FIGS. 2C and 2D, $f = 29.04$ MHz. In FIGS. 2E and 2F, $f = 29.44$ MHz. In FIGS. 2G and 2H, $f = 29.29$ MHz. In FIGS. 2A through 2G, laser power was low ($<1$kW), and nearly equal in all cases. In FIG. 2H, the laser power was $\sim 2$kW. In all cases, peak #1 was synchronous with the laser pulse to within $\sim 0.5$ μs.

The following points were noted:

(1) At resonance (29.24 MHz, FIG. 2A and B), the LOG signal consisted of a sharp positive peak at $\sim 3$ μs (peak #2), followed by a slowly varying negative component at $\sim 30$ μs (peak #4), and a much slower positive component at $\sim 150$ μs (peak #5).

(2) At a frequency slightly below resonance (29.04 MHz, FIG. 2C and D), the LOG signal consisted of an additional sharp, although weak, negative peak (#1) synchronous with the laser pulse, followed by a much stronger (as compared to peak #2 in FIG. 2A) and somewhat broadened (optical or amplifier saturation)

positive signal at ~2 μs (peak #3). This strong peak appeared to have swamped the original positive peak #2 in item (1) above. (See also item (5) below.) The initial, negative part of the slowly varying component (peak #4, now at ~50 μs) was somewhat stronger, and the final, positive component (peak #5) was broader and weaker than the same components of FIG. 2A.

(3) At a frequency slightly above resonance (29.44 MHz, FIG. 2E and F), the LOG signal consisted of the weak peak #1, now positive, followed by the strong peak #3, now negative. This strong negative peak appeared to have swamped the positive peak #2 in item (1) above. (See also item (5) below.) The peak #4 (of FIG. 2A) appeared to be neutralized by the positive overshoot of the strong negative peak #3 (see FIG. 2E). Peak #5 gained some intensity, and its maximum shifted slightly to the left (shorter times). The signal was noisy, to an extent that it increased the "start point" of the trace in FIG. 2F by almost half a division. All peaks were, however, reproducible. Note that the overall signal-to-noise ratio for the slowly varying components decreased as the rf frequency moved away from $f_o$.

(4) When the rf frequency was 29.29 MHz (FIG. 2G), peak #'s 1, 2, and 3 were not observed. Peak #4's maximum was shifted slightly to the right. However, when the laser power was increased at the same rf frequency, a sharp, fast, negative peak reappeared (FIG. 2H). The nature of this peak will be discussed below.

(5) When the rf frequency step change was smaller than that of (1)-(4) above, a gradual change of the LOG signal pattern occurred. As f decreased below $f_o$(29.24 MHz), a weak, sharp, negative peak (#1) synchronous with the laser pulse appeared, and grew slowly (FIG. 2D). Simultaneously, a positive peak #3 (unresolved from peak #2) appeared and grew rapidly on the right-hand shoulder of peak #2. This peak rapidly strengthened and engulfed peak #2, and eventually saturated the system (optical or amplifier) to produce a fairly broad, saturated peak at ~8 μs (FIG. 2D). Thus three peaks occurred in the LOG signal within ~10 μs of laser firing. On the other hand, as f gradually increased above $f_o$, a weak positive (unresolved) peak (#1) grew slowly on the left shoulder of the peak #2 (FIG. 2F); and a strong negative peak appeared and grew rapidly on the right shoulder of the same peak (#2). As f increased further, this strong negative peak engulfed the positive peak (#2), and the resulting 29.44 MHz pattern, as shown in FIG. 2F, was obtained.

(6) The delayed, broad, positive peak at ~150 μs was not inverted at any setting in (1)-(4) above. Except for FIG. 2E, a similar statement applies to the broad, negative peak at ~30 μs. In FIG. 2E, it appears that the negative nature of the peak was partly overwhelmed by the positive overshoot of the strong negative peak #3.

(7) Similar behavior was observed with the LOG signals of other $1s_j \rightarrow 2p_k$ neon excitations. However, if the metastable states $1s_5$ and $1s_3$ were not involved in the laser excitation process (either as an initial level, or as a final level after relaxation from the upper $2p_k$ level), the ~30 and ~150 μs components of the LOG signals were either nonexistent or extremely weak. In particular, the slowest component (i.e., the peak at ~150 μs), was never present in such excitations.

(8) For some excitations (e.g., $1s_2 \rightarrow 2p_2$ at 15,149.7 cm$^{-1}$), the LOG shape seemed to invert relative to the $1s_5 \rightarrow 2p_2$ signal (for the same experimental setting). In such cases, inversion of the same pair of LOG signal components occurred as the rf frequency changed from slightly below to slightly above $f_o$.

(9) A slight negative displacement (10-15 μs) of peak #5 (cf. FIG. 2A) occurred as the laser beam was displaced downward along the axis of FIG. 1 (i.e., away from electrode 6). Peak #4 also suffered a displacement of 5-10 μs. No noticeable shift of the position of peak #2 could be detected.

(10) As the rf power increased above 1 W, peaks #4 and #5 (cf. FIG. 2A) became very weak, but their null response toward a change of rf frequency remained the same as described in item (6) above. An exact nulling at $f_o$ of the frequency dependent components was then difficult, if not impossible to achieve.

Figure 3:
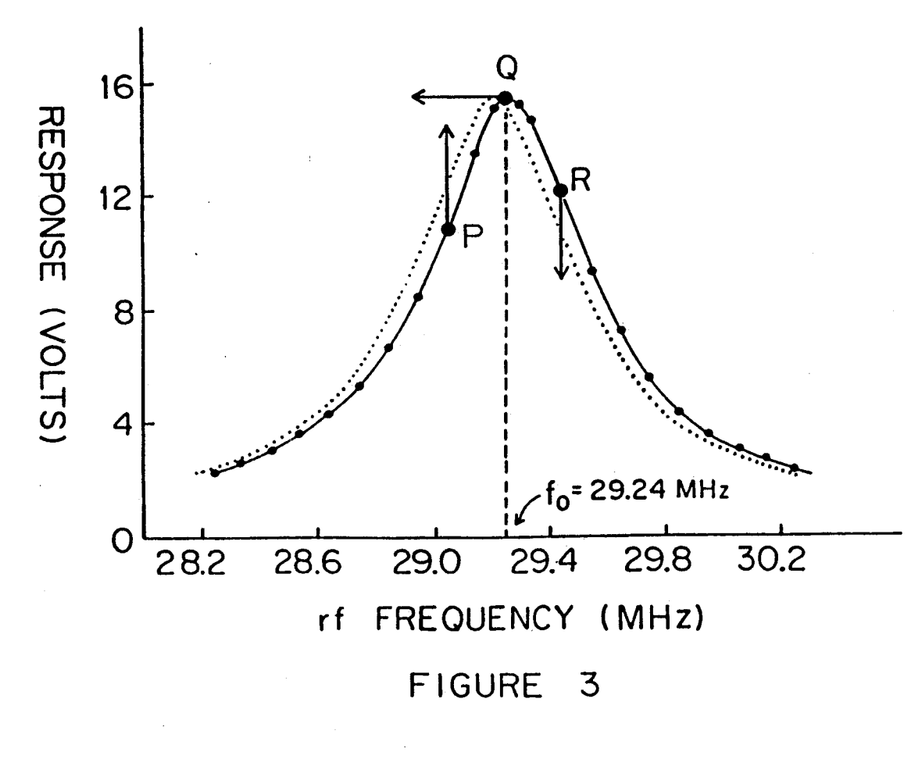
FIG. 3 illustrates the rf resonance profile of the plasma and the associated driving/detecting circuit.

The rf resonance profile of the plasma and associated driving/detecting circuit is illustrated in FIG. 3 as the solid curve. With the laser off, the rf frequency (at constant amplitude) was varied by small steps, and the corresponding response was measured by the rf carrier level, as detected in the pick-up circuit. The LOG signal, of course, was generated not by changing the rf frequency, but by laser excitation of the discharge plasma. The laser excitation, however, altered the plasma resonance characteristics. For small perturbations, the effects on LOG signal generation can be approximated by a shift of the response function of FIG. 3. For discussion purposes, three points P, Q (peak), and R are marked on the resonance profile. An increase in the equilibrium ionization rate resulting from laser excitation produced a leftward shift in the response curve, illustrated in FIG. 3 by the dotted curve. As illustrated by the corresponding arrows, this shift in the response curve caused a positive IRC signal at P, and a negative IRC signal at R. At Q, the resonance peak, the IRC signal was zero or nearly zero, because of the zero slope of the response curve at that point.

Two distinct mechanisms are involved in the generation of LOG signals. This conclusion follows from the fact that one set of peaks in the LOG temporal profile did not alter characteristics as the rf excitation frequency changed from slightly below to slightly above $f_o$, whereas another set of peaks vanished and changed polarity as the rf frequency passed through $f_o$.

We propose a simple phenomenological model for the nature of, and the observed rf frequency-dependent behavior of, the LOG signal. This model is based on two statements: (a) laser excitation of a particular transition, such as a particular $1s_j \rightarrow 2p_k$ transition, in the plasma alters the equilibrium ionization rates, with concomitant changes of the resonance characteristics (effective conductivity, capacity, and inductance); and (b) part of the energy absorbed from the laser pulse is released nonradiatively into the translational modes, and this release launches a pressure wave, or photoacoustic effect (PA effect).

On the basis of this model, one set of peaks—those that do not alter characteristics with rf frequency—are mediated by the PA effect (PAM component), whereas another set of peaks, those that are strongly rf frequency dependent, are generated by ionization rate changes (IRC component). This latter set constitutes the true LOG signal, at least in the strict sense of the word "optogalvanic." Thus at $f=f_o$, at low-to-moderate laser powers, only the PAM component is generated. At $f \neq f_o$, both mechanisms are active, and the observed LOG profile is a composite of the two signals. Because the IRC component can range from much stronger to much weaker than the PAM component, quite different signal profiles can occur in the same system under different conditions.

A. The PA-Mediated (PAM) LOG Signal

The PAM LOG signals are generated by the actual physical movement of the charged species under the influence of the PA wave. No thermal or ionization rate changes are involved in the final production step of the PAM LOG signal. Because these LOG signal components are inverted when the direction of the PA wave is reversed—reversals that could not be obtained if either thermal or ionization rate changes were involved as a final production step—it follows that such rate changes are not pertinent to these LOG components. When the rf power is increased to a few watts, the sensitive region loses definition, and very complex PAM signals may occur.

It appears that even at ~0.5 W rf power, the sensitive region (i.e., the positive ion sheath) is not confined to the close vicinity of the rf electrodes. Thus the laser pulse, in the case of neon, impinges on and excites the sensitive region of the Ne discharge. The initial PAM signal should thus not be much delayed. The initial PAM signal should, however, be followed by a slower, damped "ringing." The observed shape of these signals is discussed below. Because PAM signals are induced by the physical movement of charged species, little or no shape change is expected as the rf frequency is varied slightly about $f_o$. Some small amplitude reduction, however, should occur because the response function diminishes as f moves away from $f_o$. Because all peaks in the LOG temporal profile at $f=f_o$ (FIG. 2A) meet the above criteria, they all may be assigned to a PAM effect.

The low power rf discharge in the prior reported study of iodine, Kumar et al., "Time-Resolved Laser Optogalvanic Spectroscopy of Iodine in a Radio Frequency Discharge," J. Chem. Phys., Vol. 90 (8), pp. 4008–4014 (1989), had the advantage that the sensitive region of the discharge was confined to the vicinity of the electrodes. Because the point of laser excitation could be removed from the sensitive region, one could decipher the PAM signal by its transit time delay. At the same time, this simplicity previously prevented recognition of the powerful role that is played by the PA effect when the laser beam impinges on the sensitive region of the discharge. Both IRC and PAM effects may be involved in this case, and a LOG signal with a complex envelope may be produced. This situation appears to be the case, for example, with neon, as discussed above.

B. The Temporal Profile of the LOG signal

We now consider the time scales of the two processes and the types of relaxation shapes that may be expected.

(1) For a suitably designed system, the rise time of the LOG signal attributable to direct photoionization will be controlled by the rise time of the laser pulse. The decay time will depend on recombination/collision/diffusion rates, or on the decay time of the laser pulse, whichever is longer. Even in the case of collisional photoionization, because electron-atom/molecule collision rates are on the order of GHz or faster, the LOG signal should be synchronous with the laser pulse, and should exhibit sharp rise and fall times.

(2) If the population of a metastable level is perturbed by laser excitation, a long-lived (0.1–0.5 ms) response may be generated. Metastable levels are equilibrated primarily by collisions, and usually have long decay times. Because metastable levels play dominant roles in the maintenance of the discharge, any perturbation of their population density should produce a strong LOG signal.

(3) The laser excitation process may also release some energy in the PA channel, and a corresponding "delayed" LOG signal may be produced. If excitation occurs in the sensitive region, this delay may be of the order of a few $\mu s$ or less, depending upon gas pressure, kinetics, etc. Because acoustic signals typically have "ringing" characteristics, the leading edge of a PA-mediated signal should generally comprise a sharp, shockwave transient, followed by one or more damped overshoots.

Inspection of the signal shape in FIG. 2A indicates that the initial positive pulse was delayed a few microseconds relative to the laser pulse, and was followed by a poorly defined ringing pattern. Once perturbed by the laser pulse, which produced population density changes and initiated the PA-mediated shock wave, the recovery of discharge equilibrium involved a multitude of distinct and interrelated processes. The important factors are the kinetics of the equilibration process for various levels; the interaction between the PA wave and the excited levels; the shape and size of the discharge; and the characteristics of the electrical driving circuit. All levels with a perturbed population attain equilibrium by photon emission/absorption or collisional relaxation. To a lesser or greater extent, then, all nonequilibrated levels should contribute to the PA channel. It is therefore possible that the PA ringing component could either grow or diminish after the initial sharp PAM spike, depending on the characteristics of a given system.

The characteristics of the electrical driving circuit may also play a role in shaping the LOG signal. For example, the external ballast resistance in a DC discharge not only controls the stimulus that returns the discharge to equilibrium, but it may also affect some of the other equilibrative processes.

With the above factors in mind, and recognizing that all peaks in FIG. 2A are well-behaved with respect to a variation of f around $f_o$ (i.e., do not undergo drastic changes), we can assign the entire signal in FIG. 2A to a PA effect. Support for this attribution is provided by the temporal behavior of peaks #4 and #5 in FIG. 2A, which shifted slightly as the position of laser excitation was moved along the length of the cell. These shifts can be explained in terms of a propagation delay and/or change in the acoustic resonance pattern relative to the sensitive region of the discharge.

C. The RF Frequency-Dependent LOG Signal

We now show that the rf frequency-dependent components of LOG signals originate in changes of the equilibrium ionization rates caused by the laser excitation. The interpretation of the distinctive behavior of these components as f varies about $f_o$ is not trivial. However, because inversion crossover (i.e., nulling) occurs at $f_o$, a useful model is one with an rf/plasma resonance curve as a response/transfer function.

Any change of the equilibrium ionization rates in a discharge plasma results in concomitant changes of conductivity, capacitance, and inductance. Thus laser excitation will momentarily change the plasma resonance characteristics. For example, if the effective capacitance or inductance of the plasma increases, the resonance frequency of plasma and driving/detecting circuits should decrease. This decrease may be represented by a leftward displacement of the response curve (i.e., the dotted curve) of FIG. 3. LOG signal generation by laser-induced changes of the equilibrium ionization rates can be visualized as follows:

(1) The rf frequency values are set, say at points P, Q, or R of FIG. 3.

(2) Laser-induced changes of the equilibrium ionization rate displaces, say leftwards as illustrated, the whole resonance/response curve of FIG. 3. The amplitude of the response curve may be assumed to be invariant because there would not otherwise be a nulling at $f = f_o$.

(3) If the rf frequency is set at P, a small displacement of the resonance curve to the left will increase the response as P moves up the curve, and a positive LOG signal will result.

(4) If the rf frequency is set at R, a small displacement of the resonance curve to the left will decrease the response as R moves down the curve, and a negative LOG signal will result.

(5) If the rf frequency is set at Q (i.e., on resonance at $f = f_o$) a small displacement of the resonance curve to the left or right will not produce a significant response change, and no LOG signal will result. Thus, even though the equilibrium ionization rate changes, no LOG signal will be generated. This situation is expected only for low laser powers (i.e., for small displacements). As laser power increases, the displacement of the resonance curve may be large enough to decrease the response at $f = f_o$, and hence to produce a negative LOG signal.

(6) If the rf frequency is set at P, and if the laser excitation activates two processes which simultaneously increase and decrease the ionization rates, then these processes will generate LOG signals of opposite polarity. The process that shifts the resonance curve to the left will generate a positive LOG signal, and that which shifts the resonance curve to the right will generate a negative LOG signal. If sufficiently separated in time, two distinct signals may occur. Complementary results follow if the rf frequency is set at R.

(7) For higher power laser excitation, additional features may be observed when $f \neq f_o$. For example, if the rf frequency is set at P, a large leftward shift of the response curve may cause f to move past Q and down the right-hand side of the peak. Thus, as the laser power is gradually increased, a positive LOG signal develops, decreases, nulls, and turns negative. However, if the equilibrium ionization rate increases at a slower rate than the detection-time resolution, the corresponding LOG signal will show an initial positive component which, at its trailing edge, is followed by a negative component. Such behavior was observed in neon.

(8) Background noise is lowest at $f = f_o$, and increases on either side of $f_o$. However, the maximum of the LOG signal generated by a displacement of the response curve will occur at that point on the curve which has maximum slope. Thus the best signal-to-noise ratio for IRC components will occur at rf frequencies somewhere between $f_o$ and the point of maximum slope.

(9) If the laser excitation results in an increase in the equilibrium ionization rate, a positive IRC component is generated at P, implying that the response curve shifts to the left.

This simple model explains the behavior of the IRC component, whether induced by a change of the rf frequency or of laser power.

The origin of the two distinct rf frequency-dependent LOG signal components (i.e. two distinct changes of the equilibrium ionization rates corresponding to peaks #1 and #3) needs further elaboration. The polarities of peaks #1 and #3 indicate an initial rapid decrease of equilibrium ionization rates, followed by a slightly delayed increase of ionization rates. The mechanisms underlying those changes will now be discussed.

Laser excitation of the $1s_5 \rightarrow 2p_2$ transition in neon is followed by a relaxation of the excess population in the $2p_2$ level to all four $1s_j$ levels. The radiative transition probabilities (A) of the $2p_2$ level to levels $1s_2$, $1s_3$, $1s_4$, and $1s_5$ have been previously reported to be 2.32, 1.46, 0.561, and $1.15 \times 10^7 s^{-1}$, respectively. The $1s_3$ and $1s_5$ levels are metastable, and consequently any laser-induced population change which they suffer can equilibrate only through collisional effects. However, the decays of the $1s_2$ and $1s_4$ levels to the ground state are allowed ($A = 66.4 \times 10^7 s^{-1}$) and partially allowed ($A = 4.76 \times 10^7 s^{-1}$), respectively.

Consequently, the sequence of events after laser excitation was inferred to be as follows:

(1) The $1s_5 \rightarrow 2p_2$ laser excitation depleted the $1s_5$ metastable level population, which in turn produced an immediate decrease in the equilibrium ionization rates. At the neon pressures and the rf powers used here, Penning ionizations of the metastable levels dominated the electron impact ionization of the upper $2p_2$ level, and the equilibrium ionization rate dropped.

(2) The excited $2p_2$ population, prior to relaxation to the lower $1s_j$ levels, dissipated some energy via collisions, and initiated the events that generated the first peak of the PAM component (peak #2) and, by overshot, the somewhat broader #4 peak component. The relaxation of the $2p_2$ level was complete within a fraction of a microsecond.

(3) The vacuum ultraviolet (VUV) fluorescence from the $1s_2$ and $1s_4$ resonant levels, which acquired excess population by relaxation of the $2p_2$ level, was radiatively trapped. The effective fluorescence lifetimes of the $1s_2$ and $1s_4$ levels under these conditions are known to be $<1$ μs and $<11$ μs, respectively. The resultant VUV photons photoionized some excited entities in the discharge, and hence increased the ionization rate. Since the effective lifetime of the $1s_2$ level is less than the laser pulse width, its effects were merely superimposed on the initial set of events. A short radiation-trapped lifetime for the $1s_2$ fluorescence implies a fast escape of photons and a negligible, or very small, contribution to ionization rate changes. The $1s_4$ level, on the other hand, has a much longer effective fluorescence lifetime, and hence it contributed significantly—at least at later times—to an increase of equilibrium ionization rates (peak #3). The delay of peak #3 relative to the laser pulse ($\sim 8$ μs) is consistent with the $1s_4$ effective lifetime.

The rapid decay of peak #1 is largely attributable to swamping by peak #3, which was overwhelmingly strong and of opposite polarity.

FIG. 2G, in which an rf setting of 29.29 MHz seemed to eliminate the initial part of the PA-mediated signal, requires some comment. Because 29.29 MHz lies just above $f_o$, the first rf dependent component synchronous with the laser pulse was weak and not observed, whereas the second rf dependent component (which was negative for $f<f_o$) nearly neutralized the initial positive peak #2 of the PAM component. Slight mismatches, if any, at particular instants were buried in the noise. As the laser power increased, a larger displacement of the response curve did produce a distinct negative signal (FIG. 2H). An increase in slope of the response curve at $f(\simeq f_o)$ as Q moved away from f (due to increased ionization) resulted in a larger negative IRC component, one which more than compensated for the corresponding positive PAM peak #2.

To summarize, the various peaks in FIG. 2 can be assigned as follows: (i) Peak #'s 2, 4, and 5 in FIG. 2A and B ($f=f_o$) were pure PAM components; (ii) Peak #'s 1 and 3 were of IRC origin; (iii) Peak #'s 2, 4, and 5 in FIG. 2C-H ($f \neq f_o$) were admixtures of both PAM and IRC components. Peak #5 was predominantly PAM in nature. Peak #4 may have had some IRC component (except when the magnitudes were controlled by overshoot of strong peak #3).

Figure 4:
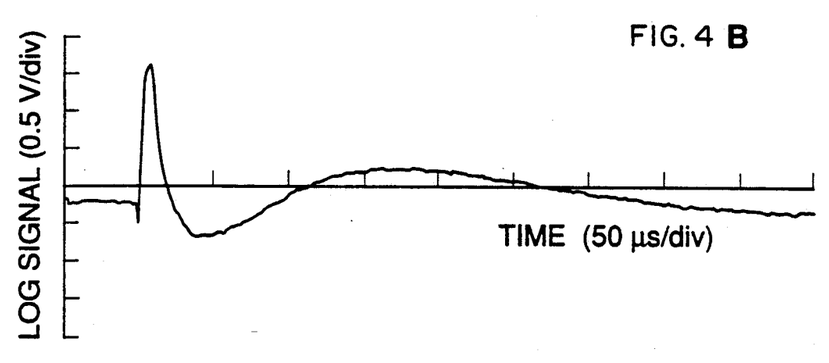
FIGS. 4A-C illustrate averaged time-resolved LOG signals in an rf discharge in neon, at or on either side of the rf resonance frequency.
Figure 4A:
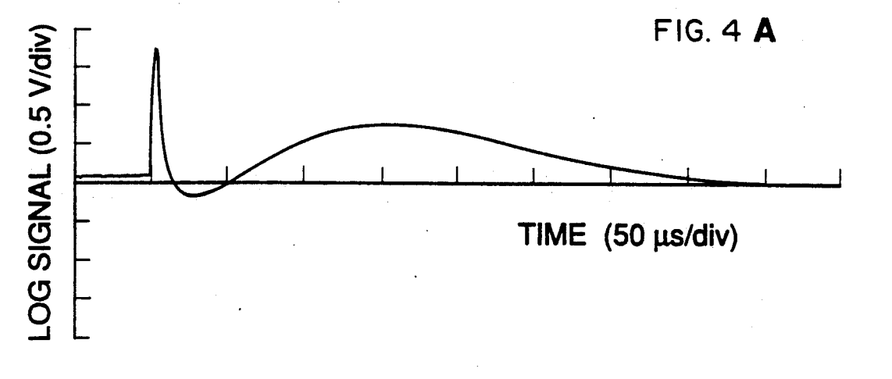

A preferred manner of separating the PAM and IRC components is to digitize several temporal profiles, and then to average those profiles. FIGS. 4A-C, for example, illustrate low-noise, averaged temporal profiles (of 100 traces each) for the same transition in neon ($1s_5 \rightarrow 2p_2$), as recorded by a digital oscilloscope (LeCroy Model 9400). FIG. 4A illustrates the averaged LOG signal at the rf resonance frequency (29.37 MHz, slightly different from that in FIGS. 2A and 2B because a slightly different rf power was used.) FIGS. 4B and 4C illustrate the corresponding LOG signals at f=29.17 MHz and f=29.57 MHz, respectively.

Figure 5:
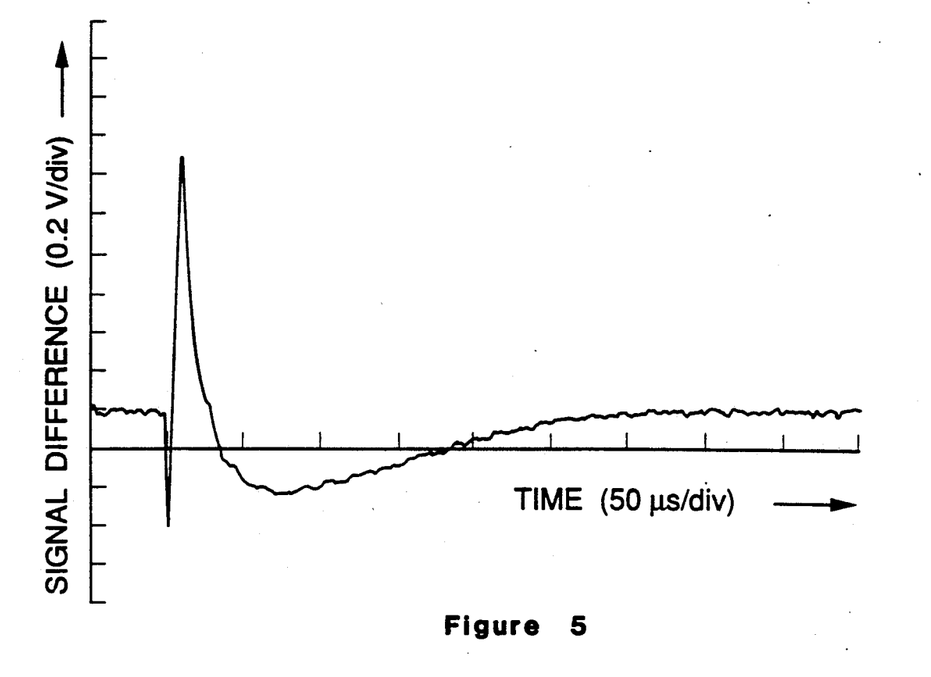
FIG. 5 illustrates the difference of the temporal profiles of FIGS. 4B and 4A.
Figure 6:
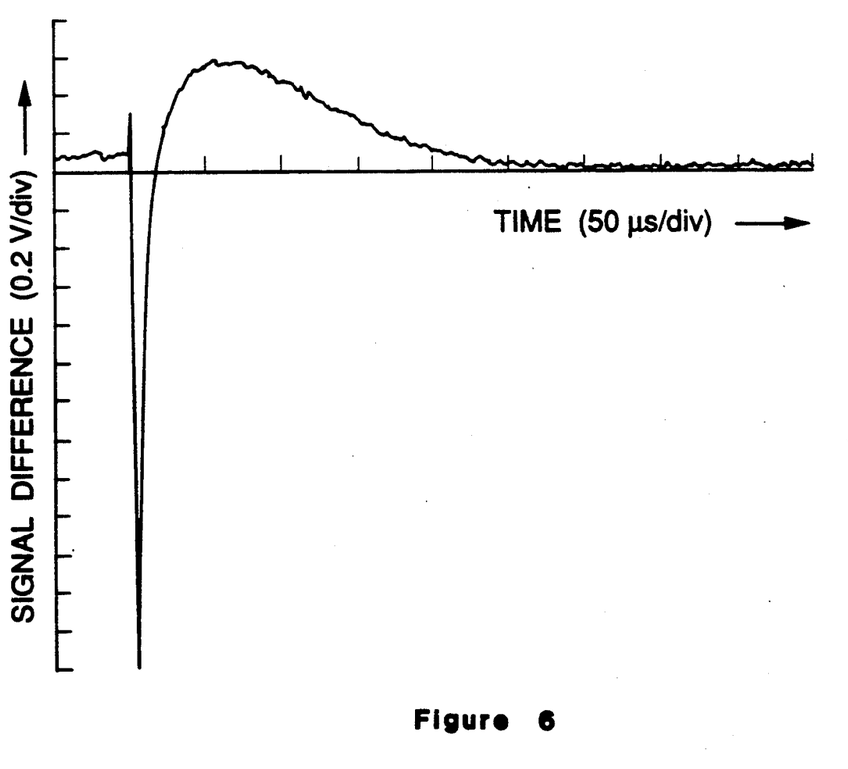
FIG. 6 illustrates the difference of the temporal profiles of FIGS. 4C and 4A.

FIG. 4A, recorded at rf resonance peak, was attributed solely to the PAM component. The IRC components were obtained by subtracting the temporal profile of FIG. 4A from that of either FIG. 4B or FIG. 4C. These differences, respectively, are illustrated in FIGS. 5 and 6. (Note that the vertical axis in FIGS. 5 and 6 is expanded relative to that of FIGS. 4A-C.) The lack of precise symmetry (peak heights) between the profiles of FIGS. 5 and 6 indicates that the response curve (analogous to that of FIG. 3) has slopes of different magnitude at points analogous to P and R. Closer symmetry would probably result by moving the points P and R closer to Q—i.e., taking the off-resonance measurements closer to the rf resonance peak.

Laser-induced changes in the equilibrium ionization rate can be estimated from the slope of the response curve at any actual operating point (such as P or R), by calibrating the shift in the response with a known (or otherwise measured) change in the ionization rate.

Although it is preferred to make measurements in accordance with this invention at the resonance frequency peak, and to compare those measurements to measurements taken at one or more other frequencies near the resonance peak, other modes of practicing this invention are possible. For example, LOG measurements could be made at two or more frequencies near (but not at) the peak, followed by an extraction of that component which varies slowly with a change in radiofrequency, and the component which varies rapidly. The former is a measure of the PAM component, and the latter, a measure of the IRC component.

Another alternative is to take a LOG measurement at low laser power at the resonance peak only, which measurement should comprise a PAM component only.

It is preferred to take multiple LOG measurements at each frequency, and to average those measurements to improve signal-to-noise ratios, as illustrated in FIGS. 4A-C.

A frequency "near" or "close to" the resonance frequency is one sufficiently close to the resonance frequency maximum to permit meaningful measurements of PAM and IRC components in accordance with this invention.

Although the use of a true pulsed laser is preferred for its better time resolution, the present invention should also work with a chopped cw laser. Therefore, references in the claims to a "pulsed laser" should be understood also to include a chopped cw laser; and reference in the claims to a "pulse" of a laser should be understood also to include a segment from a chopped cw laser beam.

The observed experimental results presented here for neon are generally similar to those which have also been observed in experiments with argon.

The entire disclosure of Kumar et al., "Role of Photoacoustics in Optogalvanics," J. Chem. Phys. Vol. 93 (6), pp. 3899-3905 (1990) (which is not prior art), is incorporated by reference.

We claim:

1. A method, in a plasma coupled by a driving circuit to a radiofrequency discharge source, for extracting from a laser optogalvanic ("LOG") signal its photoacoustic mediated ("PAM") component, comprising the steps of:
    (a) irradiating the plasma with a pulsed laser, with the radiofrequency discharge source at a first frequency equal to or close to the resonant frequency of the plasma and driving circuit;
    (b) measuring a first LOG signal as a function of time following at least one pulse of said laser irradiating, with the radiofrequency discharge source at said first frequency;
    (c) irradiating the plasma with a pulsed laser, with the radiofrequency discharge source at a second frequency equal to or close to the resonant frequency of the plasma and driving circuit; wherein said first and second frequencies are not equal;
    (d) measuring a second LOG signal as a function of time following at least one pulse of said laser irradiating, with the radiofrequency discharge source at said second frequency; and
    (e) extracting the PAM component as that part of said LOG signals which does not vary, or which varies slightly, between said first and second LOG signals.

2. A method as recited in claim 1 for additionally extracting from the LOG signal its ionization rate change ("IRC") component, additionally comprising the step of extracting the IRC component as that part of said LOG signals which varies significantly between said first and second LOG signals.

3. A method as recited in claim 2, wherein said first frequency is substantially equal to the resonant frequency peak of the plasma and driving circuit.

4. A method as recited in claim 2, additionally comprising the step of estimating the magnitude of any change in the equilibrium ionization rate of the plasma by comparing: (a) the magnitude of said IRC component to (b) a calibration of the magnitude of the IRC component with known or measured changes in ionization rates.

5. A method as recited in claim 2, wherein said method is carried out in an apparatus suitable for plasma etching.

6. A method as recited in claim 2, wherein said method is carried out in an apparatus suitable for plasma deposition.

7. A spectrometer comprising:
(a) means for generating a radiofrequency discharge plasma at a plurality of frequencies equal to or near the resonance frequency of the plasma and radiofrequency discharge;
(b) a laser having a pulsed output which can be absorbed by the plasma;
(c) means for making time-resolved measurements of the optogalvanic signal from the plasma following absorption of an output pulse from the laser; and
(d) means for determining that part of said optogalvanic signal which varies relatively slowly as the frequency of said radiofrequency discharge is varied near the resonance frequency, said slowly varying part of said optogalvanic signal being a measure of the photoacoustic mediated effect.

8. A spectrometer as recited in claim 7, additionally comprising means for determining that part of said optogalvanic signal which varies relatively rapidly as the frequency of said radiofrequency discharge is varied near the resonance frequency, said rapidly varying part of said optogalvanic signal being a measure of the ionization rate change effect.

9. An apparatus comprising:
(a) plasma etching means, and
(b) a spectrometer as recited in claim 8.

10. An apparatus comprising:
(a) plasma deposition means, and
(b) a spectrometer as recited in claim 8.

* * * * *